United States Patent [19]

Blecha et al.

[11] Patent Number: 4,955,720
[45] Date of Patent: Sep. 11, 1990

[54] ON-LINE FIBER ORIENTATION DISTRIBUTION MEASUREMENT

[75] Inventors: William E. Blecha, Cornwall-on-Hudson; Henry J. Kent, Bloomingburg, both of N.Y.

[73] Assignee: International Paper Company, Tuxedo, N.Y.

[21] Appl. No.: 293,688

[22] Filed: Jan. 5, 1989

[51] Int. Cl.$^5$ ............................................ G01N 21/86
[52] U.S. Cl. .................................. 356/429; 162/263; 250/559; 250/571
[58] Field of Search ................. 162/198, 263; 356/429, 356/432; 250/559, 571

[56] References Cited

U.S. PATENT DOCUMENTS

| | | | |
|---|---|---|---|
| 3,622,448 | 11/1971 | Adams et al. | 162/263 X |
| 4,338,024 | 7/1982 | Bolz et al. | 356/39 X |
| 4,648,712 | 3/1987 | Brenholdt | 356/432 X |

FOREIGN PATENT DOCUMENTS

| | | |
|---|---|---|
| 3413558 | 10/1985 | Fed. Rep. of Germany . |
| 610017 | 5/1978 | U.S.S.R. . |

OTHER PUBLICATIONS

Dialog Files 351 and 305; conducted Oct. 1, 13, 1987.
Lars Rudstrom and Ulf Sjolin, "A Method for Determining Fiber Orientation in Paper by Using Laser Light", Svensk Papperstidning, vol. 73, No. 5, p. 117, Mar. 15, 1970.
"An On-Line Inspection Device, Web Defect Detection with Lasers", reprinted from TAPPI, vol. 62, No. 6, p. 69, Jun. 1979.
Alois Kohl and Wolfgang Hartig, "Optical Determination of Fiber Orientation", no citation available.
Joseph A. Bolton, "Development Behind a Full Width Real Time Formation Sensor—'FORMSPEC'", no citation available.
Paul Lippke GmbH & Co., "Optical Fiber Orientation Measurement for On-Line Use".
Paul Lippke GmbH & Co., "Moisture, Basis Weight, Ash, Caliper, Opacity, Smoothness".
Intec, "Vigilant 100".
Unknown, "With a Revolutionary Defect Processing Architecture . . . ".
Robotest, "PaperLab-1".
Albany International, "WEBSPEC/Defect Detection".

Primary Examiner—Vincent P. McGraw
Attorney, Agent, or Firm—Luedeka, Hodges & Neely

[57] ABSTRACT

The present invention discloses a method and apparatus for the on-line measurement of fiber orientation in a translucent sheet. To measure the fiber orientation, coherent light is directed onto one surface of the sheet in a pattern of sufficient intensity to produce a second pattern on the other surface of the sheet. The shape of the second pattern is determined, at least in part, by the orientation of the fibers in the sheet. A sensing apparatus including a video camera and frame grabber, views the second pattern and produces a freeze frame image signal. Even though the second pattern may be moving, the sensing apparatus freezes this motion and produces the freeze frame image signal to represent a stationary image of the second pattern. The freeze frame image signal is analyzed to determine the shape of the second pattern and from this shape the orientation of the fibers in the sheet is determined. Also disclosed is an apparatus for using the method and an improved system for making paper using the method.

21 Claims, 3 Drawing Sheets

ON-LINE FIBER ORIENTATION DISTRIBUTION MEASUREMENT

FIELD OF THE INVENTION

The present invention relates to the measurement of the orientation of fibers in translucent nonwoven sheets. It also relates to improvements in making paper.

BACKGROUND OF THE INVENTION

Changes in the fiber orientation distribution of a nonwoven web cause the physical properties of the final product to vary. For example, paper may suffer from problems such as stack lean and corner to corner curl unless the mean fiber orientation distribution is uniformly in the machine direction. Also, unless the fiber orientation distribution is sufficiently random, there may be wrinkling or dimensional instabilities in the nonwoven web.

The fiber orientation distribution in paper is currently measured off-line by the zero span tensile method in a laboratory. R. J. Votava, TAPPI 65(4), 65 (1982). Small strips (usually 15 mm in width) are cut from a sample of paper in the machine direction, in the cross-direction and, depending on the accuracy required, at various angles in between. The tensile strength of each strip is then measured. Another off-line technique involves a visual count in a microscope of stained fibers. O. J. Kallmes, TAPPI 52(3), 482 (1969). Both tests are time-consuming, necessitate sample damage and require a certain degree of skill in preparing the sample.

There is another off-line method for the determination of fiber orientation by x-ray diffraction that is quicker than the zero span tensile or the microscopic measurement methods. R. E. Prud'Homme, et al., *Applied Polymer Science* 19, 2609 (1975). That method requires a prior knowledge of fibril angle distribution for accurate measurements; in addition, there is still some sample damage and some sampling skill is still needed. None of the foregoing methods are adaptable to on-line use.

A method for determining fiber orientation using laser light was introduced in 1970. L. Rudstroem, et al., *Svensk Papperstidn* 83(5), 117 (1970). When a focused coherent beam of light is transmitted through a nonwoven web, such as a sheet of paper, a diffraction pattern results which corresponds with fiber orientation. Rudstroem, et al. detected the pattern with a photomultiplier tube (PMT) behind a narrow rotating aperture. Hartig improved on that method by detecting the diffusion pattern with an arrangement of six linear photodiode arrays. W. Hartig, West German Patent DE No. 3414558, issued Oct. 24, 1985.

The laser detection methods require that the detector always be in alignment with the laser beam. When measuring wide sheets on line, the laser and detector must be independently mounted and then precisely aligned. An independent mounting may allow the laser beam to move with respect to the detector and the pattern may move out of range of the detector. This problem is further compounded by the inherent vibration involved in the manufacture of the non-woven sheet. Consequently, these methods have not been adapted to general on-line use.

Therefore, it is an object of the present invention to provide an on-line method and apparatus for detecting and analyzing the diffusion pattern of laser light transmitted through a moving sheet of nonwoven material, such as paper.

It is a further object to use that diffusion pattern to provide an on-line determination of the fiber orientation distribution in the moving sheet of nonwoven material.

It is another object of the present invention to provide an improved method for manufacturing paper.

SUMMARY OF THE INVENTION

The present invention provides for a method and apparatus for the on-line measurement of the fiber orientation distribution in moving nonwoven sheets. In the present invention, a laser beam that is incident at right angles to the plane of a translucent nonwoven web sheet is focused to a first pattern which is a circular spot with a diameter of around 150 micrometers at the sheet surface. As the beam passes through the sheet, fibers in the sheet causes a distortion of the beam to form a second pattern of elliptical shape on the other sheet surface. The major axis of the ellipse is oriented in the average direction of the orientation of the fibers. The ratio of the length of the major axis to the length of the minor axis is representative of the distribution of the fiber orientation.

The ellipse is preferably magnified by a lens to around 1 millimeter approximate diameter and a video camera is used to sense the ellipse. The video camera has field of view that is very much larger than the size of the ellipse. Therefore, the ellipse can experience large perturbations of position (in a preferred embodiment for example, on the order of five to ten times the dimensions of the ellipse) due to misalignment or machine vibration without leaving the field of view of the video camera. Also, the image of the ellipse is devised to freeze the motion of the ellipse so that vibration or other motion caused by the environment will not prevent the operation of the apparatus. A single frozen image of the ellipse is obtained either by means of a shutter, by controlling the laser to produce a burst of light or by sampling and storing a single frame of the video camera image. This single image becomes a freeze frame signal which is analyzed for major and minor axis lengths that are used to determine the degree of fiber orientation in the sheet. The angle of the major axis corresponds to the mean fiber orientation in the sheet.

In a preferred embodiment, the laser and video camera are mounted to traverse the width of the sheet in order to monitor the entire sheet for fiber orientation. Alternatively, a set of mirrors may be used to direct the laser beam and/or the second pattern image to and from various portions of the moving sheet. Again, since the field of view of the video camera is very much larger than the image, misalignment problems between the laser and video camera are minimized.

Changes in the second pattern image intensity may be caused by weight variations in and flutter of the nonwoven sheet. These intensity variations are corrected by monitoring the size of the ellipse and adjusting the laser power by means of a feedback circuit. The controller for adjusting the laser power may be made responsive to other aspects of the image such as a size or shape of the second pattern.

Further, in accordance with a preferred embodiment, the manufacturing processes involved in making translucent non-woven sheets, such as paper, may be adjusted to provide a desired fiber orientation distribution. Using paper manufacture as an example, the headbox section of a papermaking machine may be controlled to adjust the rate of flow and/or distribution of the pulp suspension to the forming sheet or wire. The rate of flow and/or distribution is directly related to the fiber orientation; varying the rate would vary the orientation. If the orientation of the fibers is not as desired, then the headbox rate of flow and/or distribution is adjusted until the orientation is of the proper angle and distribution. Other variables in papermaking can be controlled (such as deckle position, rush/drag ratio, tapered header recirculation or slice edge bleed) to produce the desired fiber orientation and distribution.

BRIEF DESCRIPTION OF THE DRAWINGS

The present invention may be best understood by reference to the following detailed description of an exemplary embodiment when considered in conjunction with the drawing in which.

DETAILED DESCRIPTION OF THE DRAWINGS

Figure 1:
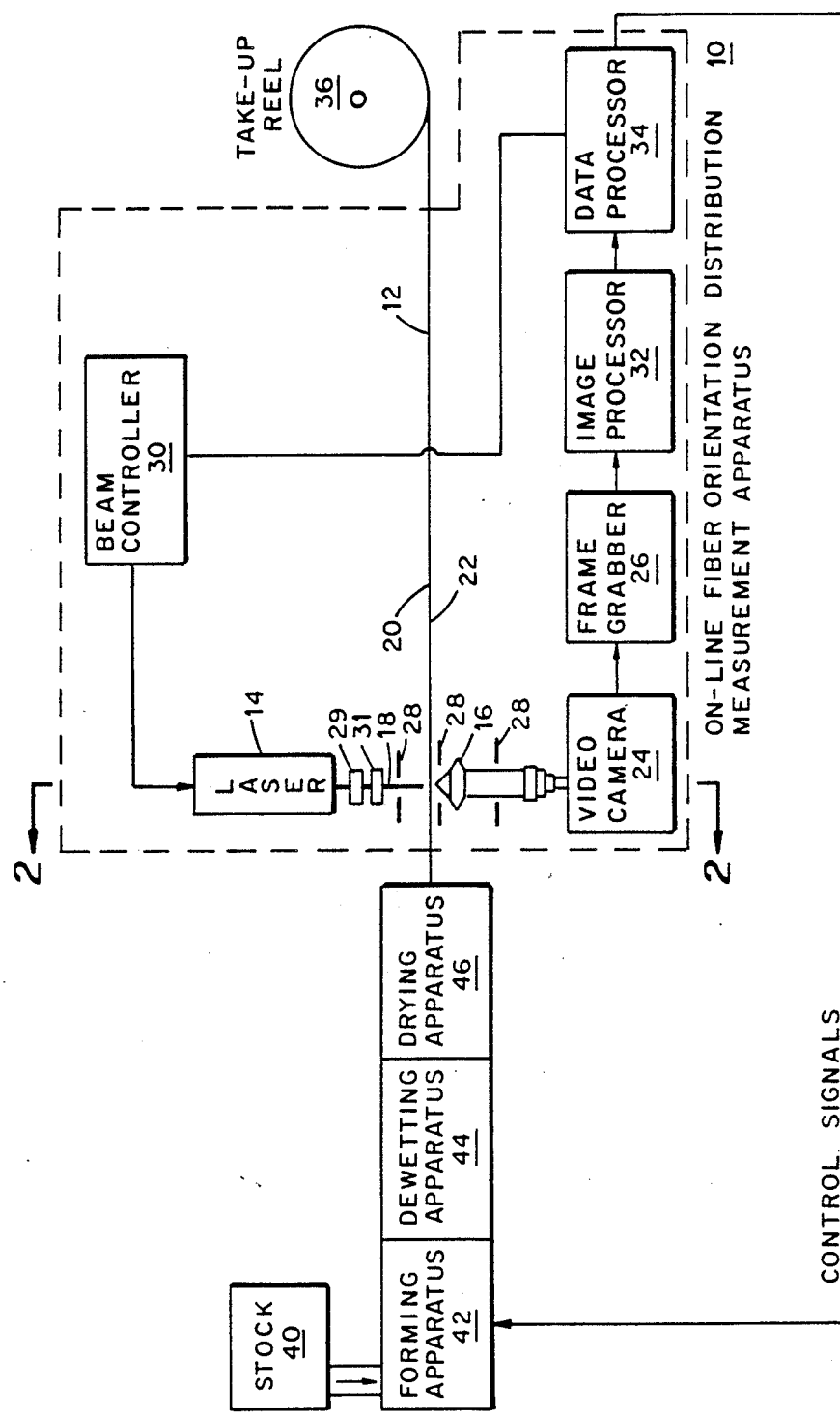
FIG. 1 is a block schematic diagram of an apparatus for the on-line measurement of fiber orientation distribution in use with a papermaking system.

Referring now to the drawing in which like reference characters designate like or corresponding parts throughout the several views, there is shown in FIG. 1 an apparatus for the on-line measurement of fiber orientation distribution 10 embodying the present invention. A sheet 12 of nonwoven material moves between a laser 14 and a lens 16. A beam 18 from the laser 14 is directed onto a first surface 20 of the sheet 12 by a beam compressor 29 and collimator 31. The beam forms a first pattern on the first surface 20 that is circular in shape and about 150 micrometers in diameter. The laser beam 18 is perpendicular to the first surface 20. As the beam 18 passes through the sheet 12 from the first surface 20 to the second surface 22, the light is distorted by the fibers in the sheet 12. When the beam 18 emerges from the second surface 22, it forms a second pattern on the second surface 22 that is elliptical in shape.

The shape and orientation of the ellipse is related to the fiber orientation distribution in the sheet 20. A random distribution of fiber orientations will give a circular second pattern. An ellipsoidal second pattern indicates a non-random mean orientation. The orientation of the major axis of the ellipse gives the direction of the mean orientation and the ratio of the major axis to the minor axis gives the distribution of the orientation (i.e. the relative number of fibers in the mean orientation).

The lens 16 magnifies the second pattern to about 1 millimeter in diameter, and a video camera 24 senses the magnified second pattern. The field of view of the camera 24 is very much larger than the 1 millimeter second pattern; preferably on the order of five to ten times the largest diameter of the second pattern.

Since the image of the second pattern may be moving around in the field of view of the camera 24, a freeze frame of the image signal over a very short period of time is produced. The freeze frame period of time must be sufficiently long to allow the camera 24 to produce an image signal, but it must also be sufficiently short to freeze the image when the image is moving at or below a predetermined velocity within the field of view. A freeze frame may be produced with a frame grabber 26, with shutters 28, with a beam controller 30 or with a combination of the above. The frame grabber 26 samples the image signal from the camera 24 and stores a single frame (sampling one complete frame scan in a standard video camera). Shutters 28, which may be on either side of the sheet 20, would allow the beam 18 to be transmitted or the second pattern to be received by the camera 24 for the freeze frame period of time. The beam controller 30 would produce a burst of laser light for the freeze frame period of time. The shutter speed or the freeze frame speed varies according to application. In some applications the freeze frame speed need only be about 1/30 of a second and the freeze function may be performed solely by the frame grabber. To achieve freeze frame speeds on the order of 1/200 second or 1/1000 second, shutters are preferred.

The freeze frame image signal is sent to an image processor 32 where the fiber orientation distribution is determined. The direction of movement of the sheet 12 is known. The freeze frame image signal of the second pattern has a major axis and a minor axis. The processor 32 determines the length and direction of the major and minor axes of the image. The angle between the direction of movement of the sheet 12 and the major axis is the mean orientation of the fibers in the sheet; the ratio between the lengths of the major and minor axes indicate the fiber orientation distribution, or the degree of fiber alignment in the direction of the mean orientation. The fiber orientation and distribution information is then sent to a data processor 34 for further processing.

As the sheet 12 moves relative to the camera 24, the intensity of the second pattern may vary with weight variations or other changes in the sheet 12. A feedback system is employed to maintain the second pattern at a desired intensity. The data processor 34 monitors the intensity of the second pattern image signal from the camera 24. When the intensity of the image signal varies, the processor 34 generates a feedback signal to the controller 30; the controller 30 then adjusts the laser 14 to vary the intensity of the beam 18 to maintain a desired intensity of the second pattern. The second pattern image signal monitored by the processor 34 may be a freeze frame signal or a continuous signal.

The on-line measurement of the fiber orientation distribution is used as a part of a control system in an automatic papermaking apparatus. The sheet 12 moves through the on-line apparatus 10 and then, eventually, onto a take-up reel 36. The sheet 12 is produced when a papermaking pulp solution from a stock 40 is fed into a forming apparatus 42. The forming apparatus 42 may be one of a number of different systems. For example, it may consist of a Fourdrinier and headbox or a "Vertiforma" machine. A web or sheet 12 is formed in the forming apparatus 42, dewatered in a dewatering apparatus 44 and dried in a drying apparatus 46.

The data processor 34 generates control signals for use in the forming apparatus 42 to control the orientation and distribution of the fibers in the paper. Since the forming apparatus 42 may be one of a number of different systems, the control signals of the data processor 34 are adapted for use in the particular forming apparatus 42 to be used. For example, the control signals may control deckle position, rush/drag ratio, tapered header recirculation or slice edge bleed in a fourdrinier forming apparatus.

Figure 2:
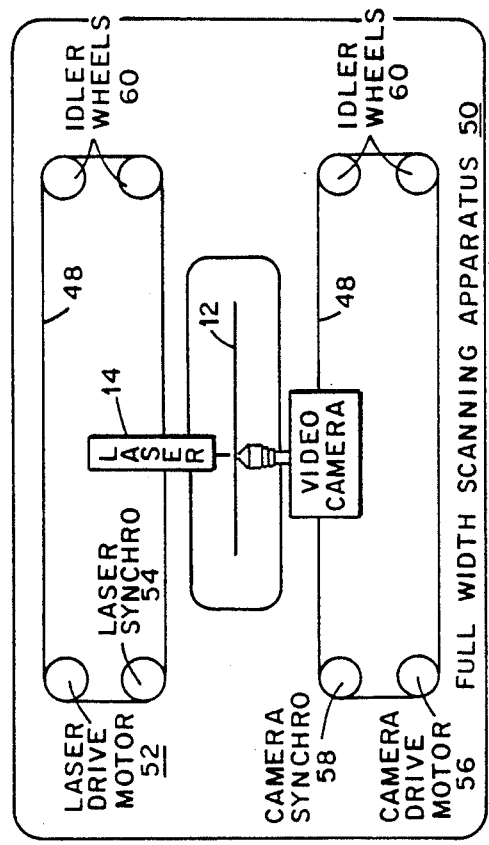
FIG. 2 is a diagram of a preferred embodiment of a means for moving a video camera and a laser across the width of a moving sheet.

The video camera 24 and the laser 14 may be mounted to be moved across the width of the moving sheet 12. In FIG. 2 there is shown a diagram of a preferred embodiment of a means for moving the video camera 24 and the laser 14 with respect to the moving sheet 12. The camera 24 and laser 14 are mounted on the movable belts 48 of a full width scanning apparatus 50. Each belt 48 is mounted independently of the other belt 48. The belt 48 associated with the laser 14 is driven across the surface of the sheet 12 by the laser drive motor 52. The position of the laser 14 with respect to the width of the sheet 12 is measured by the laser synchro 54. A similar arrangement is provided for the belt 48 associated with the video camera 24. The camera drive motor 56 positions the video camera 24 across the width of the sheet 12. The position of the video camera 24 with respect to the width of the moving sheet 12 is monitored with the camera synchro 58. Idler wheels 60 maintain tension on the belts 48.

The laser 14 and the video camera 24 are maintained in rough alignment by the laser synchro 54 and the camera synchro 58. This rough alignment is sufficient to maintain the second pattern on the second side 22 of the moving sheet 12 within the field of view of the video camera 24. Small perturbations in the alignment of the laser 14 and the video camera 24 will be dealt with as described above in relation to the discussion of the frame grabber 26, image processor 32 and data processor 34.

It will be appreciated that this is but one illustration of a way in which the laser 14 and the video camera 24 may be mounted so that they may measure the entire width of the moving sheet 12. Many modifications may be made to the apparatus as described which will not depart from the scope of the invention. For example, moving mirrors may be used to direct the laser beam 18 or the view of the video camera 24 to various parts of the moving sheet 12; or, the laser 14 and the camera 24 may be mounted on a chain drive apparatus.

Figure 3:
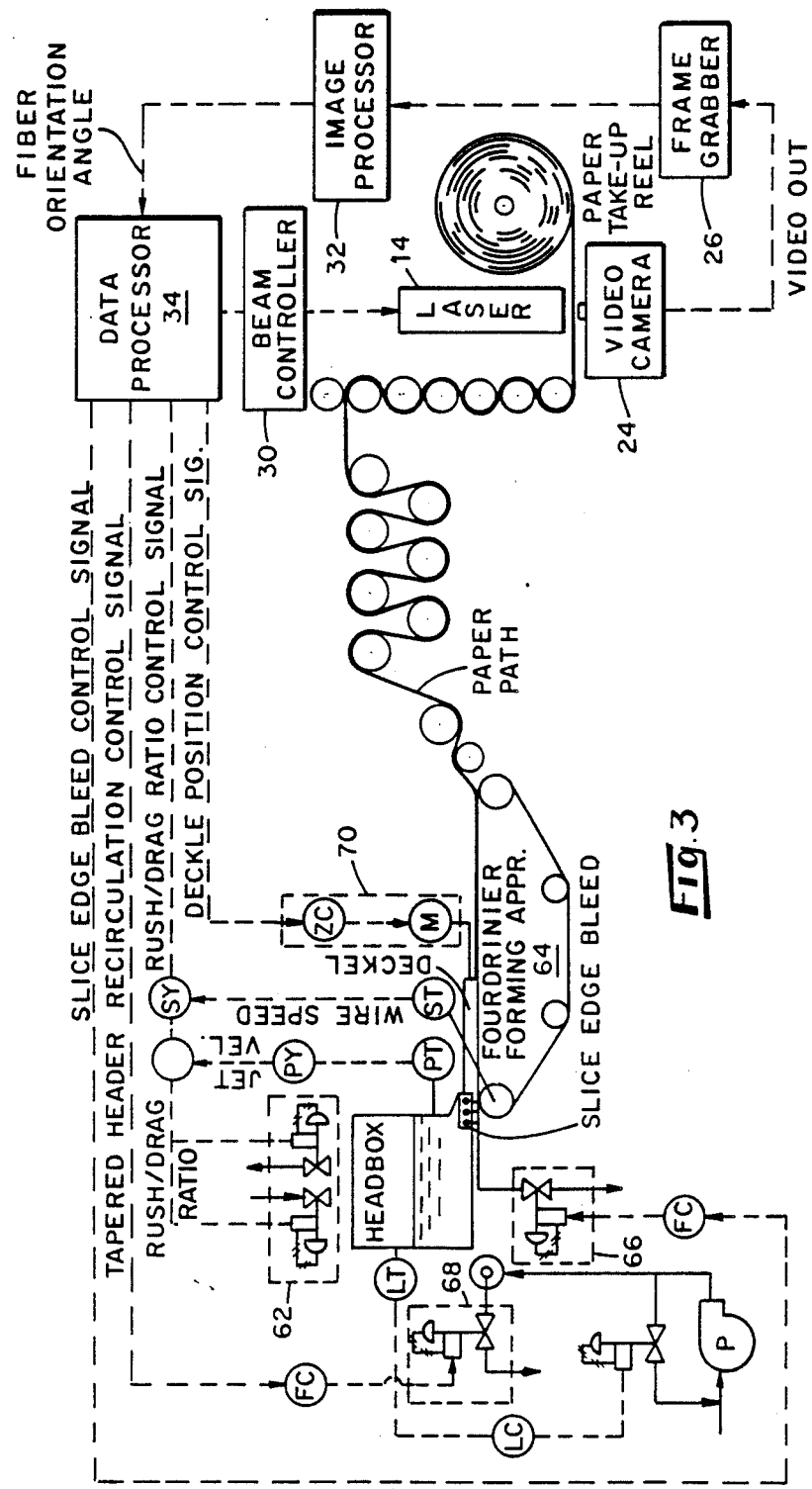
FIG. 3 is a schematic diagram of the present invention in use with a fourdrinier paper forming apparatus.

Regardless of the specific type of forming apparatus 42, it responds to the control signals to achieve a desired fiber orientation. Using a fourdrinier forming apparatus as shown in FIG. 3, if the fibers of the sheet 12 are oriented too much in the machine direction, the data processor 34 may send a control signal to the rush/drag ratio control 62 in the fourdrinier forming apparatus 64 to decrease the rush/drag ratio. In addition, control signals may be sent to the slice edge bleed control 66, the tapered header recirculation control 68 or the deckle position control 70. These are examples of how control signals from the data processor 34 to the forming apparatus 64 may be used to vary fiber orientation.

From the foregoing, it may be seen that the present invention provides for the on-line measurement of fiber orientation distribution in the moving web of nonwoven material. The present invention also provides an improved method for manufacturing paper. The foregoing description of the drawing is intended as an example of the invention. It is understood that the invention is capable of numerous modifications, rearrangements and substitutions of parts without departing from the scope of the invention as set forth in the claims.

What is claimed is:

1. An on-line fiber orientation measurement system for measuring the orientation of fibers in a translucent sheet at least in part composed of fibers, said sheet having a first surface and a second surface, said system comprising:
   a source of coherent light for producing and directing a first light pattern onto said first surface of said sheet, said first light pattern having an intensity sufficient to transmit light through said sheet and form a second light pattern on the second surface, the shape of the second light pattern being dependent at least in part on the fiber orientation in the sheet;
   a sensor for sensing said second pattern displayed on said second surface, said sensor further comprising video camera means for producing an image signal corresponding to an image of said second pattern and having a field of view that is substantially larger than the second pattern whereby relative movement of the source and sensor within a predetermined range will move the second light pattern through a range that is totally within the field of view of said camera;
   means for producing a freeze frame of said image signal, said freeze frame being representative of the image of said second pattern during a period of time that is sufficiently long to allow the camera to produce an image signal and is sufficiently short to freeze the image of the second light pattern when it is moving at or below a predetermined velocity within the field of view; and
   means for analyzing the shape of the second light pattern in the freeze frame to determine the orientation of fibers.

2. The system of claim 1 wherein said means for producing a freeze frame further comprises means for controlling said source of coherent light to produce a single burst of light for each freeze frame.

3. The system of claim 1 wherein said means for producing a freeze frame further comprises a shutter between said source of coherent light and said first pattern on said first surface.

4. The system of claim 1 wherein said means for producing a freeze frame signal further comprises a shutter between said second surface and said sensor.

5. The system of claim 1 wherein said means for producing a freeze frame further comprises means for sampling and storing a single frame from said camera during a period of time that is at least sufficient for said camera to produce an image signal.

6. The system of claim 1 wherein said first pattern is a circle and said second pattern is an ellipse with a major axis and a minor axis.

7. The system of claim 6 wherein the means for determining the orientation of fibers further comprises:
   means for identifying and determining the orientation of the major axis of said ellipse and for producing an output signal corresponding to the major axis orientation to thereby indicate the fiber orientation of the sheet.

8. The system of claim 7 wherein said means for determining the orientation of fibers further comprises:
   means for determining the length of said major axis of said ellipse;
   means for determining the length of said minor axis of said ellipse; and
   means for comparing the length of said major axis with the length of said minor axis and for producing a comparison signal indicating a fiber orientation distribution.

9. The system of claim 1 further comprising:
   feedback circuit means for receiving said image signal and producing a feedback signal corresponding to said second light pattern; and controller means responsive to the feedback signal for controlling said source of coherent light to adjust the intensity of said first pattern.

10. The system of claim 1 further comprising means for scanning said source of coherent light and said sensor in conjunction across the width of the sheet to determine the orientation of fiber at a plurality of locations along said width of said sheet.

11. In a system for making paper in an environment of noise and vibration, the system having a papermaking pulp solution from stock, said pulp solution being fed into a forming apparatus, forming a web, said web being dewatered in a dewatering apparatus and dried in a drying apparatus, said web then becoming a moving sheet, said moving sheet having a first surface and a second surface and having a direction of motion and a width perpendicular to said direction of motion, wherein the improvement comprises:

a source of coherent light for producing and directing a first light pattern onto said first surface of said moving sheet, said first light pattern having an intensity sufficient to transmit light through said sheet and form a second light pattern on the second surface, the shape of the second light pattern being dependent at least in part on the fiber orientation in the sheet;

a sensor for sensing said second pattern produced on said second surface, said sensor and light source being subjected to the noise and vibration of the environment such that relative movement exists between said source and said sensor whereby said second pattern moves at or below a predetermined velocity and within a predetermined range relative to said sensor;

said sensor further comprising video camera means for producing an image signal corresponding to an image of said second pattern and said camera means having a field of view that is substantially larger than the second pattern whereby the relative movement of the source and sensor will move the second light pattern through the predetermined range that is totally within the field of view of said camera;

means for producing a freeze frame of said image signal, said freeze frame being representative of said second pattern during a period of time that is sufficiently long to allow the camera to produce an image signal and is sufficiently short to freeze the image of the second light pattern when it is moving at or below the predetermined velocity within the field of view;

means for analyzing the shape of the second light pattern to determine the orientation of fibers; and means for generating control signals, said control signals controlling the forming apparatus until said means for determining the orientation of fibers in said sheet determines a desired orientation of fibers.

12. The system of claim 11 wherein said means for producing a freeze frame further comprises means for controlling said source of coherent light to produce a single burst of light for each freeze frame produced.

13. The system of claim 11 wherein said means for producing a freeze frame further comprises a shutter between said source of coherent light and said first surface.

14. The system of claim 11 wherein said means for producing a freeze frame further comprises a shutter between said second surface and said sensor.

15. The system of claim 11 wherein said means for producing a freeze frame further comprises means for sampling and storing a single frame from said camera during a period of time that is at least sufficient for said camera to produce an image signal.

16. The system of claim 11 wherein said first pattern is a circle and said second pattern is an ellipse with a major axis and a minor axis.

17. The system of claim 16 wherein the means for determining the orientation of fibers further comprises:

means for determining the direction of motion of said moving sheet;

means for identifying the major axis of said ellipse and for determining the direction of the major axis; and means for comparing the direction of motion of said sheet with the direction of the major axis and for determining the orientation of said fibers in said sheet relative to the direction of motion.

18. The system of claim 17 wherein the means for determining the orientation of fibers further comprises:

means for determining the length of said major axis of said ellipse;

means for determining the length of said minor axis of said ellipse; and means for comparing the length of said major axis with the length of said minor axis and for producing a comparison signal indicating a fiber orientation distribution.

19. The system of claim 11 further comprising means for controlling said source of coherent light whereby the intensity of said first pattern may be adjusted.

20. The system of claim 11 further comprising:

means for controlling said source of coherent light to adjust the intensity of said first pattern; and wherein said sensor further comprises feedback circuit means that generates a feedback signal for said means for controlling said source of coherent light and adjusting the intensity of said second pattern.

21. The system of claim 11 further comprising means for moving said source of coherent light and said sensor in conjunction to determine the orientation of fibers in said moving sheet at selected positions along the width of said sheet.

* * * * *